(12) United States Patent
Ito et al.

(10) Patent No.: US 8,110,146 B2
(45) Date of Patent: Feb. 7, 2012

(54) EMBEDDED BLOCK HUMIDIFIER, AUTOMATIC THIN SLICE MANUFACTURING DEVICE, AND AUTOMATIC THIN SLICE SPECIMEN MANUFACTURING APPARATUS

(75) Inventors: Tetsumasa Ito, Chiba (JP); Yukimitsu Kijima, Chiba (JP); Koji Fujimoto, Chiba (JP)

(73) Assignee: Seiko Instruments Inc., Chiba (JP)

( * ) Notice: Subject to any disclaimer, the term of this patent is extended or adjusted under 35 U.S.C. 154(b) by 505 days.

(21) Appl. No.: 12/275,610

(22) Filed: Nov. 21, 2008

(65) Prior Publication Data
US 2009/0137028 A1    May 28, 2009

(30) Foreign Application Priority Data

Nov. 27, 2007   (JP) ................................. 2007-306353
Aug. 22, 2008   (JP) ................................. 2008-214344

(51) Int. Cl.
*G01N 21/00*   (2006.01)

(52) U.S. Cl. ........... 422/63; 422/65; 422/68.1; 422/500; 436/180

(58) Field of Classification Search .............. 422/63–67, 422/68.1, 500; 436/180
See application file for complete search history.

(56) References Cited

U.S. PATENT DOCUMENTS
5,231,029 A * 7/1993 Wootton et al. ............ 435/303.2

FOREIGN PATENT DOCUMENTS
JP       2004-028507 A    1/2004

* cited by examiner

*Primary Examiner* — Jyoti Nagpaul
(74) *Attorney, Agent, or Firm* — Brinks Hofer Gilson & Lione (57) ABSTRACT

An embedded block is capable of being humidified in a short time without influencing a surface temperature of the embedded block as much as possible. An embedded block humidifier for humidifying an embedded block having a biological specimen embedded in an embedding agent is provided which includes a vapor generating mechanism for generating vapor heated at a predetermined temperature and a guiding mechanism for guiding the vapor to the embedded block so that the generated vapor contacts with a surface of the embedded block set at a predetermined standby position.

9 Claims, 9 Drawing Sheets

EMBEDDED BLOCK HUMIDIFIER, AUTOMATIC THIN SLICE MANUFACTURING DEVICE, AND AUTOMATIC THIN SLICE SPECIMEN MANUFACTURING APPARATUS

RELATED APPLICATIONS

This application claims priority under 35 U.S.C. §119 to Japanese Patent Application Nos. JP2007-306353 filed on Nov. 27, 2007, and JP2008-214344 filed on Aug. 22, 2008, the entire contents of which are hereby incorporated by reference.

BACKGROUND

1. Technical Field

The present invention relates to an embedded block humidifier for humidifying an embedded block having a biological specimen embedded in an embedding agent, an automatic thin slice manufacturing device for automatically manufacturing a thin slice by slicing the humidified embedded block, and an automatic thin slice specimen manufacturing apparatus for automatically manufacturing a thin slice specimen in which the manufactured thin slice is fixed onto a substrate.

2. Related Art

In the past, a toxicity test, a pathology test, or the like using a laboratory animal is carried out before a clinical trial for new drug development. Such test and experiment are carried out by using a thin slice specimen in which a thin slice having a thickness of several μm (for example, 3 to 5 μm) is fixed onto a plate such as a slide glass. The thin slice is obtained in such a manner that a laboratory animal such as a mouse or a rabbit receiving a drug is subjected to an autopsy and is sliced for the pathology test. Additionally, the thin slice is manufactured for each of various parts (for example, brain, lung, and the like).

A microtome is known as a device for manufacturing such thin slice specimen. Here, a general method of manufacturing a thin slice specimen using the microtome will be described.

First, moisture of a formalin-fixed biological specimen such as an organism or an animal is replaced with paraffin and again the periphery thereof is solidified by paraffin, thereby manufacturing an embedded block in a block shape. Subsequently, the embedded block is set at a microtome as a slicing device to be subjected to a roughing cut process. In terms of the roughing cut process, the surface of the embedded block becomes flat, and the surface of the embedded biological specimen as an experiment or observation object is exposed.

After the roughing cut process ends, a main cutting process starts. This main cutting process corresponds to a process in which the embedded block is cut into an ultra thin slice having the above-described thickness by a cutting blade of the microtome. Accordingly, it is possible to obtain the thin slice. At this time, since the embedded block is cut into the ultra thin slice as thin as possible, a thickness of the thin slice is approximately identical with a thickness of a cell level, thereby obtaining a thin slice specimen having higher quality. Accordingly, it is required to manufacture a thin slice having a smaller thickness. Additionally, the main cutting process is repeated until obtaining a necessary sheet of thin slice.

Subsequently, an extending process is carried out in which the thin slice obtained by the main cutting process is extended. That is, since the thin slice manufactured by the main cutting process is cut into the ultra thin slice, the thin slice is in a wrinkling state or a rounding state (for example, in a U-shape). For this reason, it is necessary to remove the wrinkling or rounding of the thin slice to be thereby extended in terms of the extending process.

In general, the extending process is carried out by the use of water and warm water. First, the thin slice obtained by the main cutting process is floated on water. Accordingly, it is possible to remove the wrinkling or rounding of the thin slice while preventing paraffin embedding the biological specimen from being adhered to each other. Subsequently, the thin slice is floated on warm water. Accordingly, since the thin slice is easily extended, it is possible to remove the remaining wrinkling or rounding not completely removed during the extending process using water.

Subsequently, the thin slice subjected to the extending process using warm water is lifted up by the use of a substrate such as a slide glass to be placed on the substrate. Additionally, when the extended degree is not sufficient at this time point, the substrate is heated by being placed on a hot plate or the like. Accordingly, it is possible to more extend the thin slice.

Finally, the substrate having the thin slice placed thereon is dried in a dryer. In terms of the drying process, moisture attached to the thin slice during the extending process evaporates and the thin slice is fixed onto the substrate. As a result, it is possible to manufacture the thin slice specimen.

Incidentally, when the surface of the embedded block is dry upon manufacturing the thin slice, a problem may arise in that wrinkle or deformation occurs in a slice surface. For this reason, it is necessary to carry out an operation in which the embedded block is prevented from being dried. That is, it is necessary to prevent the embedded block from being dried by appropriately humidifying the embedded block.

Therefore, as an example of embedded block humidifying devices, Patent Document 1 discloses an embedded block humidifying device in which misty droplet (hereinafter, referred to as mist) is generated in terms of ultrasonic vibration and an embedded block is humidified by the mist.
[Patent Document 1] JP-A-2004-28507

However, the humidifying device according to the related art still has a problem to be solved.

Figure 12:
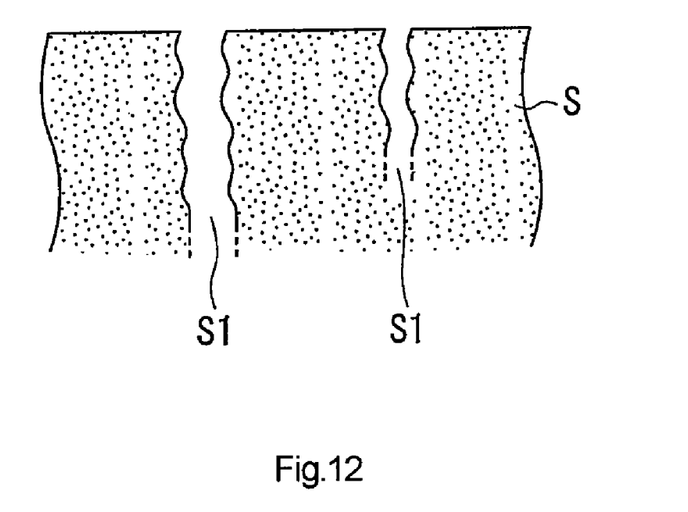
FIG. 12 is an enlarged diagram showing the surface of the embedded block.

First, the embedded block will be simply described. In general, paraffin having a water repellent property is used as an embedding agent embedding a biological specimen. Additionally, since moisture of the biological specimen itself is replaced with paraffin, its surface has a water repellent property. Incidentally, as shown in FIG. 12, countless gaps S1 are formed in a surface of a biological specimen S in which moisture is replaced with paraffin. Accordingly, in order to humidify the embedded block, it is necessary to humidify the biological specimen S from the inside in terms of the countless gaps S1.

Figure 13:
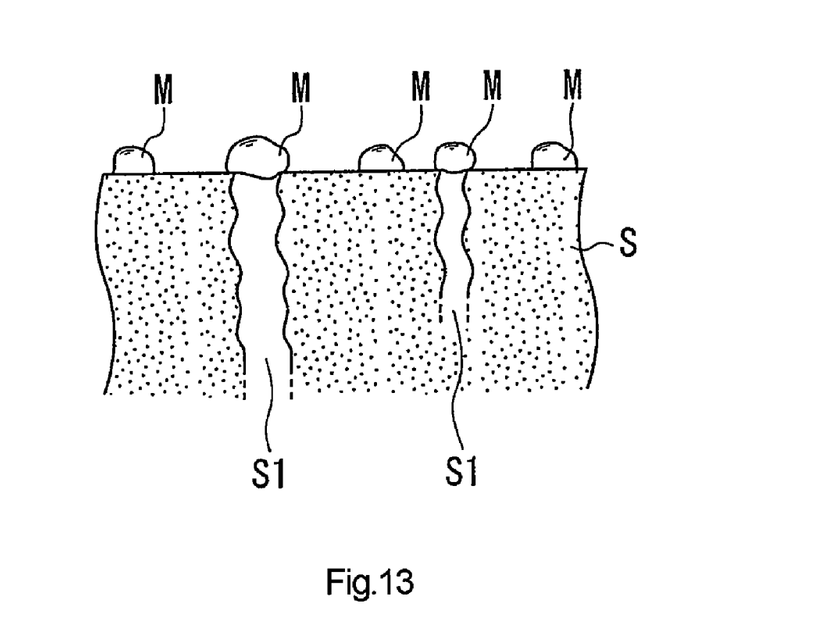
FIG. 13 is a diagram showing a humidification method according to the related art and a state where mist (misty water droplet) is attached to the surface of the embedded block shown in FIG. 12.

Incidentally, each of the countless gaps S1 corresponds to a minute gap having a diameter of several hundreds nm to 1 μm or so. For this reason, as shown in FIG. 13, even when mist M is generated and attached to the surface of the embedded block, in many cases, the mist M bounces on an entrance of the gap S1 due to the influence of surface tension. Accordingly, the mist M cannot easily enter into the gap S1, and hence it requires much time to allow the mist M to enter thereinto.

Meanwhile, when an amount of mist increases in order to reduce a time necessary for the humidification, another problem arises. That is, in a case where the amount of mist increases, an excessive amount of mist M is attached to the surface of the embedded block. Then, the surface temperature of the embedded block reduces by 2° C. or so due to evaporative latent heat generated when an excessive amount of mist M evaporates, thereby causing a problem in that thermal contraction occurs in the embedded block. As a result, a problem arises in that a deviation in thickness of the thin slice obtained by slicing the embedded block occurs.

SUMMARY OF THE INVENTION

The present invention is contrived in consideration of the above-described problems, and an object of the invention is to provide an embedded block humidifier capable of humidifying an embedded block in a short time without influencing a surface temperature of the embedded block as much as possible, an automatic thin slice manufacturing device having the embedded block humidifier, and an automatic thin slice specimen manufacturing apparatus having the automatic thin slice manufacturing device.

In order to achieve the above-described object, the invention adopts the following configuration.

According to an aspect of the invention, there is provided an embedded block humidifier for humidifying an embedded block having a biological specimen embedded in an embedding agent, the embedded block humidifier including: a vapor generating mechanism generating vapor heated at a predetermined temperature; and a guiding mechanism guiding the vapor to the embedded block so that the generated vapor contacts with a surface of the embedded block set at a predetermined standby position.

In the embedded block humidifier according to the invention, when the embedded block is set at the standby position, the guiding mechanism guides the vapor generated by the vapor generating mechanism to the embedded block and sprays the vapor to contact with the surface of the embedded block. Particularly, unlike the mist used in the related art, since the embedded block is exposed to the vapor as gas, the vapor easily enters into a minute gap formed in the surface of the biological specimen in which moisture is replaced with paraffin. At this time, since the vapor is heated at a predetermined temperature, when the vapor enters into the gap and contacts with the biological specimen, the vapor therein becomes a condensed state. Accordingly, it is possible to wet the biological specimen from the inside. As a result, it is possible to humidify the embedded block.

Particularly, since the vapor as gas is used, even when the gap is minute, it is possible to reliably allow the vapor to enter into the gap. Accordingly, it is possible to humidify the embedded block in a short time. Additionally, since the vapor enters into the gap, it is possible to sufficiently carry out the humidification by the use of a small amount of vapor. Accordingly, it is possible to prevent a problem of the related art that the temperature reduction of the embedded block caused by the excessive evaporation of mist occurs. As a result, it is possible to humidify the embedded block in an optimal state while preventing the thermal contraction of the embedded block and thus to manufacture a high-quality thin slice.

In the embedded block humidifier with the above-described configuration, the vapor generating mechanism may include: a tank storing liquid; a liquid heater heating the liquid; a heater temperature controller controlling a temperature of the liquid heater; a bubble generating mechanism provided with a pipe inserted into the tank to be submerged in the liquid and generating countless bubbles from the front end of the pipe by supplying air to the pipe; and an air controller controlling an air supply amount.

In the embedded block humidifier according to the invention, when air is supplied to the pipe of the bubble generating mechanism, countless bubbles are generated from the front end of the pipe under the liquid stored in the tank. Then, since the countless bubbles contact with the peripheral liquid, an air-liquid interface is formed therebetween. At this time, since the liquid is heated by the liquid heater, the liquid evaporates in the gas in the bubbles via the air-liquid interface to thereby humidify the gas. Particularly, since the size of each of the bubbles is small and the surface area thereof becomes large relative to the volume, the gas in the bubbles is approximately humidified up to the saturated vapor pressure in a short time. For this reason, when the countless bubbles bounce on the water surface, the vapor heated at a predetermined temperature is generated in the tank. With such a simple configuration, it is possible to reliably generate the vapor. Additionally, since it is possible to control the liquid heater by the use of the heater temperature controller, it is possible to control the temperature of the vapor at a desired temperature by freely controlling the temperature of the liquid. Accordingly, it is possible to reliably humidify the embedded block by the use of the vapor.

Additionally, since it is possible to control the air supply amount supplied to the pipe by the use of the air controller, it is possible to appropriately control the amount of the generated vapor. Accordingly, it is possible to reliably carry out the humidification while restricting a variation in surface temperature of the embedded block as much as possible.

In the embedded block humidifier with the above-described configuration, the humidifier further includes a sensor measuring a surface temperature of the embedded block, and the heater temperature controller may control the temperature of the liquid heater so that a temperature of the generated vapor more increases than a temperature of the embedded block measured by the sensor by a predetermined temperature.

In the embedded block humidifier according to the invention, since the sensor is provided, it is possible to accurately measure the surface temperature of the humidified embedded block. Then, the heater temperature controller is capable of controlling the temperature of the liquid heater on the basis of the surface temperature of the embedded block so that the temperature of the vapor more increases than the temperature of the embedded block by a predetermined temperature. Accordingly, it is possible to prevent a case in which the embedded block is exposed to the vapor having a temperature larger than the temperature of the embedded block. As a result, it is possible to reliably humidify the embedded block by the use of the vapor while restricting a temperature variation of the embedded block.

In the embedded block humidifier with the above-described configuration, the air controller may control the air supply amount on the basis of the temperature of the embedded block measured by the sensor.

In the embedded block humidifier according to the invention, since the air controller controls the air supply amount supplied to the pipe on the basis of the surface temperature of the embedded block, it is possible to prevent a case in which the embedded block is too much exposed to the excessive vapor and hence the temperature thereof varies. Accordingly, it is possible to more reliably restrict the temperature variation of the embedded block.

In the embedded block humidifier with the above-described configuration, the guiding mechanism may include: a guiding pipe guiding the vapor to the embedded block; a guiding-pipe heater heating the guiding pipe; and a guiding-pipe temperature controller controlling a temperature of the guiding-pipe heater.

In the embedded block humidifier according to the invention, the vapor generated by the vapor generating mechanism is guided to the embedded block via the inside of the guiding pipe. At this time, since the guiding pipe is heated by the guiding-pipe heater, it is possible to heat the vapor passing therethrough. Accordingly, even when the guiding pipe is configured as a long pipe, it is possible to prevent a case in which the temperature of the vapor becomes lower than the temperature of the embedded block.

Accordingly, it is possible to freely design the guiding pipe and to reliably humidify the embedded block. Additionally, since it is possible to freely control the temperature of the guiding-pipe heater by the use of the guiding-pipe temperature controller, it is possible to reliably guide the vapor to the embedded block while keeping the temperature of the vapor at a predetermined temperature.

In the embedded block humidifier with the above-described configuration, the guiding mechanism may include: an accumulating part temporarily accumulating the vapor and a discharging mechanism discharging the accumulated vapor to the outside of the accumulating part at a time; and the guiding mechanism guides the discharged vapor to the embedded block.

In the embedded block humidifier according to the invention, when the guiding mechanism guides the vapor generated by the vapor generating mechanism to the embedded block, the accumulating part temporarily accumulates the vapor therein. Then, after a predetermined amount of vapor is accumulated, the guiding mechanism discharges the accumulated vapor to the outside of the accumulating part by the use of the discharging mechanism and guides the discharged vapor to the embedded block. Accordingly, since it is possible to supply the vapor accumulated up to a certain degree to the embedded block, it is possible to carry out the humidification in a shorter time. Accordingly, it is possible to improve the throughput and thus to manufacture the thin slice having higher quality.

According to another aspect of the invention, there is provided an automatic thin slice manufacturing device including: the embedded block humidifier according to the invention; a fixed table placing and fixing the embedded block thereon; a cutting mechanism provided with a cutting blade disposed at a position away from the standby position and cutting the embedded block by moving the fixed table between the standby position and the cutting blade so as to obtain a thin slice having a predetermined thickness; and a thin slice carrying mechanism carrying the cut thin slice.

In the automatic thin slice manufacturing device according to the invention, first, the embedded block is placed and fixed onto a placement table in terms of a manual operation or a robot. Then, when the fixed table is moved by the cutting mechanism and the placed embedded block is set at the standby position, the embedded block humidifier starts to humidify the embedded block. Accordingly, while the embedded block is located at the standby position, the embedded block is humidified in an optimal state where a temperature variation hardly occurs.

Subsequently, the cutting mechanism cuts the embedded block by moving the fixed table toward the cutting blade so as to obtain a sheet-like slice having a predetermined thickness (for example, 5 μm). Accordingly, it is possible to manufacture the cut thin slice. Then, the manufactured thin slice is carried by the thin slice manufacturing device. In this manner, it is possible to automatically carry the thin slice to the subsequent process in a sequential order.

Particularly, since the embedded block is humidified in an optimal state where the temperature variation hardly occurs, it is possible to manufacture the thin slice having a uniform thickness by restricting a deviation in thickness. Accordingly, it is possible to manufacture a high-quality thin slice. Additionally, since it is possible to humidify the embedded block in a short time, it is possible to reduce a time necessary for the humidification and thus to improve the throughput.

In the automatic thin slice manufacturing device with the above-described configuration, the device further includes: a position sensor determining whether the embedded block is located at the standby position; and a controller operating the vapor generating mechanism when the position sensor determines that the embedded block is located at the standby position.

In the automatic thin slice manufacturing device according to the invention, when the embedded block is located at the standby position, the position sensor outputs position information to the controller. Then, the controller receives the position information, and operates the vapor generating mechanism. Accordingly, it is possible to promptly humidify the embedded block located at the standby position. Particularly, since the embedded block humidifier is not operated meaninglessly, it is possible to save power and thus to easily reduce running cost.

In the automatic thin slice manufacturing device with the above-described configuration, the cutting mechanism may move the fixed table after a predetermined elapsed time from a time point when the vapor generating mechanism is operated.

In the automatic thin slice manufacturing device according to the invention, since the cutting mechanism manufactures the thin slice by moving the fixed table after a predetermined elapsed time from a time point when the vapor generating mechanism is operated, it is possible to manufacture the thin slice from the embedded block optimally humidified all the time. Accordingly, it is possible to more reliably manufacture the high-quality thin slice.

According to still another aspect of the invention, there is provided an automatic thin slice specimen manufacturing apparatus including: the automatic thin slice manufacturing device according to the invention; a block carrying mechanism carrying the embedded block onto the fixed table; an extending mechanism extending the thin slice carried by the thin slice carrying mechanism by floating the thin slice on at least liquid; and a transferring mechanism manufacturing a thin slice specimen by transferring the extended thin slice onto a substrate.

In the automatic thin slice specimen manufacturing apparatus according to the invention, since the block carrying mechanism is provided, it is possible to simply and easily carry a plurality of embedded blocks onto the fixed table in a sequential order. Additionally, the thin slice carried by the thin slice carrying mechanism is extended by being floated on liquid such as water included in the extending mechanism. Accordingly, wrinkling or rounding of the thin slice generated during the cutting process is removed in terms of surface tension, thereby extending the thin slice. Then, the extended thin slice is transferred onto the substrate such as a slide glass by the use of the transferring mechanism. Accordingly, it is possible to manufacture the thin slice specimen in which the thin slice is transferred onto the substrate.

Particularly, since the thin slice manufactured by the automatic thin slice manufacturing device is the high-quality thin slice having a uniform thickness as much as possible, it is possible to manufacture a high-quality thin slice specimen. Accordingly, it is possible to more improve precision upon carrying out various experiments and tests using the thin slice specimen.

In the embedded block humidifier according to the invention, it is possible to humidify the embedded block in a short time in an optimal state without influencing the surface temperature of the embedded block as much as possible.

Further, in the automatic thin slice manufacturing device according to the invention, since the embedded block humidifier is provided, it is possible to manufacture the thin slice having a uniform thickness from the embedded block by restricting a deviation in thickness. Accordingly, it is possible to manufacture the high-quality thin slice. Additionally, since it is possible to humidify the embedded block in a short time, it is possible to reduce a time necessary for the humidification and thus to improve the throughput.

Furthermore, in the automatic thin slice specimen manufacturing apparatus according to the invention, since the automatic thin slice manufacturing device is provided, it is possible to manufacture the high-quality thin slice specimen. Accordingly, it is possible to more improve precision upon carrying out various experiments and tests using the thin slice specimen.

DETAILED DESCRIPTION OF THE PREFERRED EMBODIMENTS

First Embodiment

Hereinafter, a first embodiment of the invention will be described with reference to FIGS. 1 to 6. Additionally, in the present embodiment, a biological tissue S extracted from a laboratory animal such as a mouse is exemplified as a biological specimen.

An automatic thin slice specimen manufacturing apparatus 1 according to the present embodiment is an apparatus for manufacturing a thin slice specimen H by transferring a thin slice B1 manufactured from an embedded block B having the biological tissue S embedded in an embedding agent onto a slide glass (substrate) G.

Figure 1:
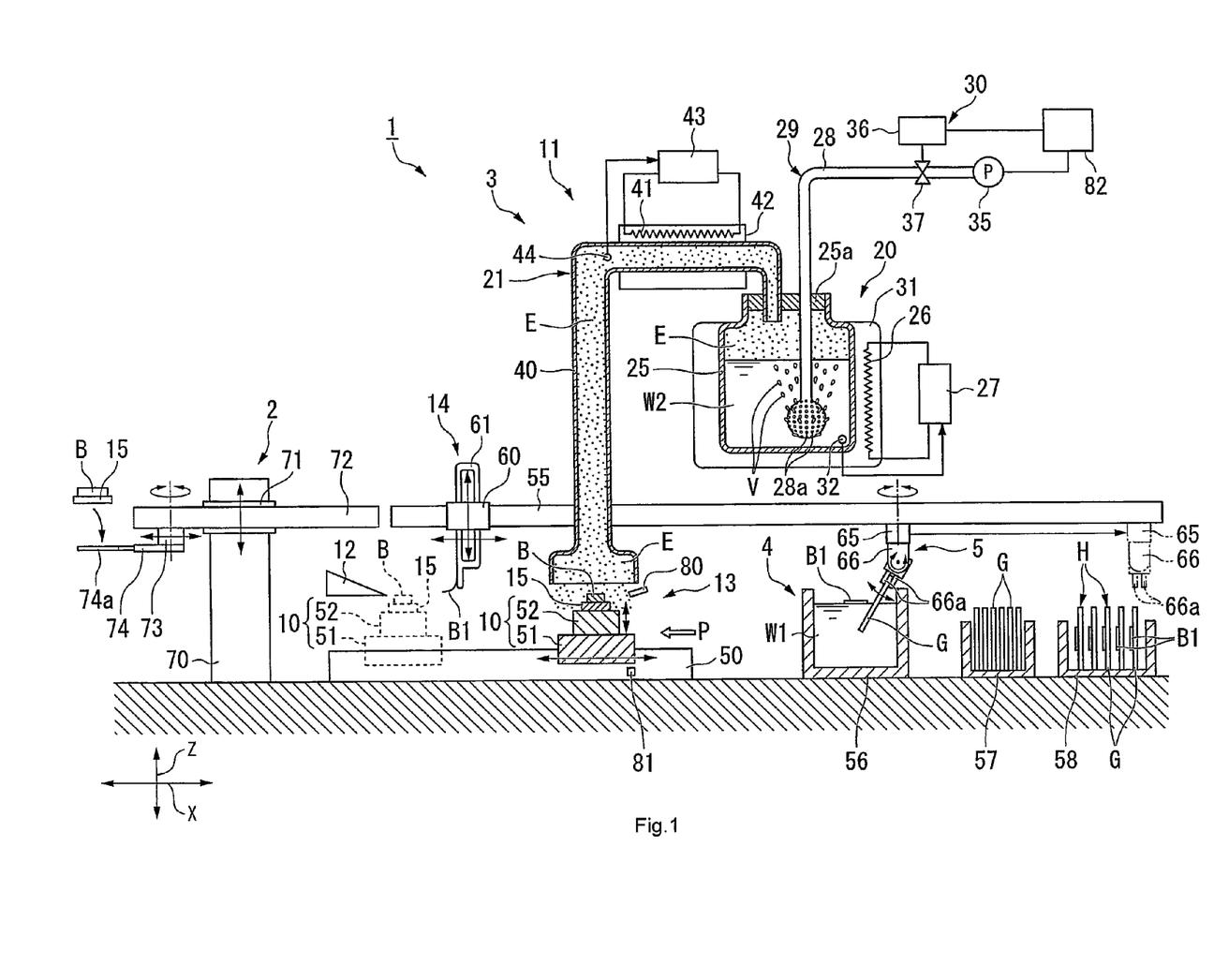
FIG. 1 is a configuration diagram showing an automatic thin slice specimen manufacturing apparatus according to a first embodiment of the invention.

As shown in FIG. 1, the automatic thin slice specimen manufacturing apparatus 1 includes a block handling robot (block carrying mechanism) 2 for carrying the embedded block B onto a fixed table 10, an automatic thin slice manufacturing device 3 for manufacturing the thin slice B1 from the carried embedded block B, an extending mechanism 4 for extending the thin slice B1 carried by a slice handling mechanism (thin slice carrying mechanism) 14 of the automatic thin slice manufacturing device 3 by floating the thin slice B1 on at least water (liquid) W1, and a slide glass handling robot (transferring mechanism) 5 for manufacturing the thin slice specimen H by transferring the extended thin slice B1 onto the slide glass G.

The automatic thin slice manufacturing device 3 is a device for cutting the embedded block B into the sheet-like thin slice B1 having a predetermined thickness.

That is, the automatic thin slice manufacturing device 3 includes the fixed table 10 for placing and fixing the embedded block B carried by the block handling robot 2, an embedded block humidifier 11 for humidifying the embedded block B fixed onto the fixed table 10 at a standby position (a position indicated by the arrow P), a cutting mechanism 13 provided with a cutting blade 12 disposed at a position away from the standby position and cutting the embedded block B by moving the fixed table 10 between the standby position and the cutting blade 12 so as to obtain the thin slice B1, and the slice handling mechanism 14 for carrying the cut thin slice B1.

Figure 2:
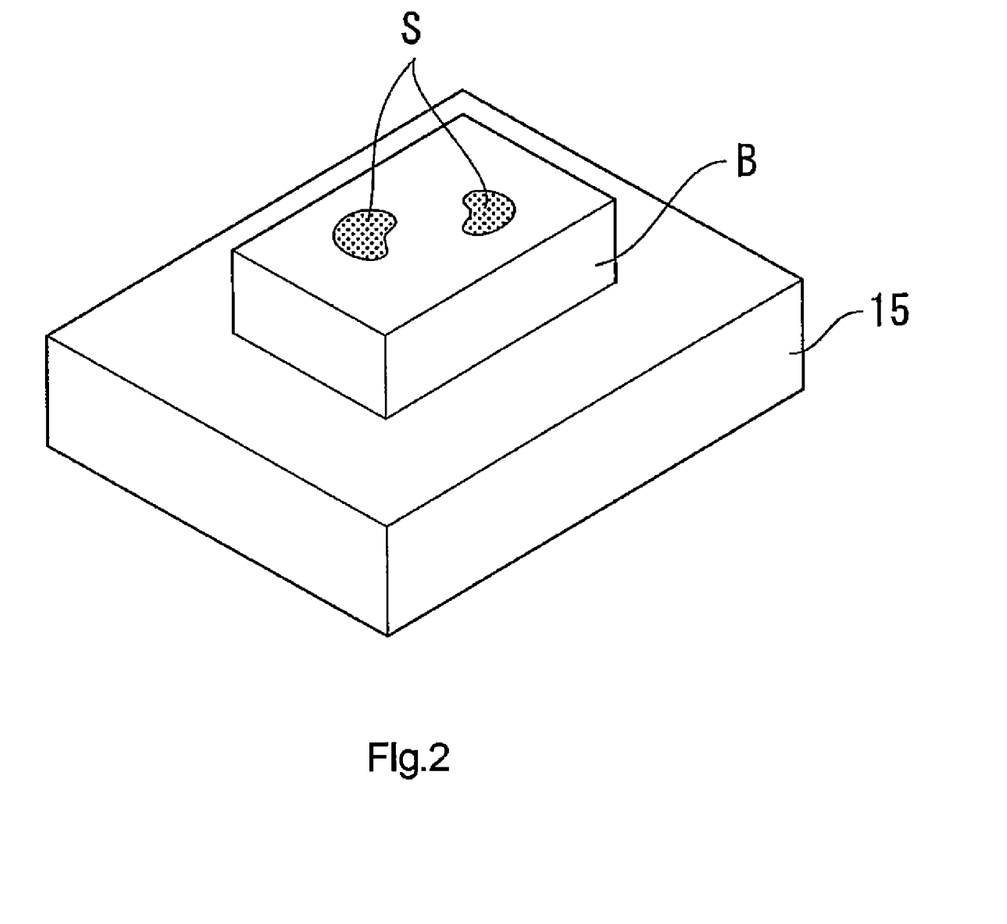
FIG. 2 is a perspective diagram showing an embedded block used in the automatic thin slice specimen manufacturing apparatus shown in FIG. 1.

As shown in FIG. 2, the embedded block B is formed in such a manner that moisture in the formalin-fixed biological tissue S is replaced with paraffin and again the periphery thereof is solidified in a block shape in terms of an embedding agent such as paraffin. Accordingly, the biological tissue S is embedded in paraffin.

As shown in FIG. 1, the embedded block B formed in this manner is placed and fixed onto a cassette 15 fixed onto a Z-stage 52 described below. Then, the embedded block B is configured to reciprocate between the standby position and the cutting blade 12 in terms of the movement of the X-stage 51 described below.

The embedded block humidifier 11 includes a vapor generating mechanism 20 for generating vapor E heated at a predetermined temperature and a guiding mechanism 21 for guiding the vapor E to the embedded block B so that the generated vapor E contacts with the surface of the embedded block B set at a standby position.

The vapor generating mechanism 20 includes a tank 25 for storing water (liquid) W2, a heater (liquid heater) 26 for heating the water W2 stored in the tank 25, a temperature controller (heater temperature controller) 27 for controlling a temperature of the heater 26, a bubble generating mechanism 29 provided with a pipe 28 inserted into the tank 25 to be submerged in the water W2 and generating countless bubbles from the front end of the pipe 28 by supplying air to the pipe 28, and an air controller 30 for controlling an air supply amount.

The tank 25 is configured such that the upper portion is mounted with an air-tight member 25a and the inside is maintained in an air-tight state. The tank 25 is configured such that the peripheral portion is surrounded by a rubber heat 31 having therein the heater 26. The heater 26 is electrically connected to the temperature controller 27 so that a heating amount is controlled. The temperature controller 27 controls the heating amount of the heater 26 on the basis of the measurement result output from a temperature sensor 32 mounted to the inside of the tank 25. Accordingly, it is possible to set a temperature of the water W2 stored in the tank 25 to a constant temperature (for example, 40° C.).

Additionally, the temperature controller 27 is configured to receive a surface temperature of the embedded block B from a temperature sensor 80 described below. Then, the temperature controller 27 is configured to control the temperature of the water W2 stored in the tank 25 by controlling the temperature of the heater 26 so that a temperature of the vapor E generated in the tank 25 increases more than the received surface temperature of the embedded block B by a predetermined temperature (for example, +2° C.).

The pipe 28 is configured such that the front end is submerged in the water W2 stored in the tank 25 via the air-tight member 25a and the base end is connected to an air supply source 35 such as an air compressor disposed at a position away from the tank 25. The pipe 28 and the air supply source 35 serve as the bubble generating mechanism 29.

An electromagnetic valve 37 for being opened or closed by an opening-closing controller 36 is provided in the pipe 28 between the air supply source 35 and the tank 25. That is, the electromagnetic valve 37 is configured to be opened or closed so as to control an air supply amount supplied from the air supply source 35 on the basis of a signal of the opening-closing controller 36. That is, the electromagnetic valve 37 and the opening-closing controller 36 serve as the air controller 30.

Additionally, like the temperature controller 27, the opening-closing controller 36 is configured to receive the surface temperature of the embedded block B from the temperature sensor 80. Then, the opening-closing controller 36 controls the air supply amount on the basis of the surface temperature of the embedded block B. Additionally, the vapor E in the tank 25 is generated in proportion to the air supply amount.

The front end of the pipe 28 is substantially formed in a spherical shape, and the surface is provided with countless minute openings 28a. For this reason, air passing through the pipe 28 is discharged to the outside via the countless minute openings 28a upon arriving at the front end. Accordingly, countless bubbles V are generated in the water. Additionally, since the water W2 stored in the tank 25 is heated by the heater 26, the water W2 is maintained in a heated state until the countless bubbles V rise to the water surface. Accordingly, gas in the bubbles V is in a heated state. For this reason, the vapor E heated at a predetermined temperature is generated in the tank 25 when the countless bubbles V bounce on the water surface.

The air supply source 35 and the opening-closing controller 36 of the vapor generating mechanism 20 with such a configuration are operated by a controller 82 described below.

Here, in addition to the pipe 28, a base end of a guiding pipe 40 is inserted into the tank 25 via the air-tight member 25a. At this time, the guiding pipe 40 is inserted in the tank 25 so as not to contact with the water W2 stored in the tank 25. Then, the guiding pipe 40 extends so that the front end is located at a position in the vicinity of the embedded block B set at the standby position. At this time, the front end of the guiding pipe 40 is formed in a shape in which the end is widened, and is set so as to cover the embedded block B set at the standby position from the upside.

Likewise, since the guiding pipe 40 is set between the tank 25 and the embedded block B, the vapor E generated in the tank 25 is guided to the embedded block B via the guiding pipe 40, and is sprayed to the surface of the embedded block B.

Incidentally, the rubber heater 42 having therein the heater (guide-pipe heater) 41 is mounted to a portion in the course of the guiding pipe 40 so as to cover the peripheral portion of the guiding pipe 40. The heater 41 is electrically connected to a temperature controller (guide-pipe temperature controller) 43 so that a heating amount is controlled. The temperature controller 43 controls the heating amount of the heater 41 on the basis of the measurement result output from a temperature sensor 44 mounted to the inside of the guiding pipe 40. Accordingly, it is possible to guide the vapor E to the embedded block B in a state where the temperature of the vapor E passing through the guiding pipe 40 is equal to the temperature of the vapor E upon being generated in the tank 25.

The guiding pipe 40, the heater 41, and the temperature controller 43 described above serve as the guiding mechanism 21.

Incidentally, the fixed table 10 for fixing the embedded block B includes an X-stage 51 capable of moving along a guide rail 50 extending in an X direction toward the cutting blade 12 and a Z-stage 52 capable of moving in a Z direction toward a vertical direction while being mounted onto the X-stage 51.

The guide rail 50 is mounted so as to extend to a position exceeding the cutting blade 12. The X-stage 51 is configured to reciprocate on the guide rail 50 in terms of a motor or the like (not shown). Additionally, the Z-stage 52 is provided with a piezo element or the like (not shown) so that the height is controlled to increase by a predetermined amount in a Z direction upon being applied with a voltage. At this time, the Z-stage 52 is controlled to move up by a predetermined amount whenever the X-stage 51 reciprocates the guide rail 50.

Accordingly, the embedded block B placed and fixed onto the Z-stage 52 via the cassette 15 moves toward the cutting blade 12 in accompany with the movement of the X-stage 51 to be thereby cut by the cutting blade 12. At this time, since the height is controlled by the Z-stage 52, the surface is cut by a predetermined thickness (for example, 5 μm). As a result, the sheet-like thin slice B1 is manufactured. The sheet-like thin slice B1 will be described later in detail. Additionally, in terms of reciprocating motion of the X-stage 51 and moving-up motion of the Z-stage 52 synchronized with the reciprocating motion, a plurality of thin slices B1 is sequentially manufactured from the embedded block B. The guide rail 50, the X-stage 51, the Z-stage 52, and the cutting blade 12 constitute the cutting mechanism 13.

A horizontal guide rail 55 extending in an X direction like the guide rail 50 is mounted to a portion above the fixed table 10 by the use of a support portion (not shown). Additionally, at a position below the horizontal guide rail 55, there are provided a reservoir 56 for storing the water (liquid) W1, a slide glass containing shelf 57 for containing an unused slide glass G, and an containing shelf 58 for containing the manufactured thin slice specimen H in a sequential order from the guide rail 50.

Additionally, the horizontal guide rail 55 is mounted with a horizontal stage 60 capable of moving along the horizontal guide rail 55. Then, the horizontal stage 60 is mounted with an arm portion 61 capable of moving in a Z direction and having the front end capable of adsorbing the thin slice B1 cut from the embedded block B by the use of, for example, static electricity. Additionally, instead of the static electricity, the thin slice B1 may be adsorbed by the use of adsorbing force, adhesive, or the like.

The arm portion 61 is configured to carry the adsorbed thin slice B1 to the reservoir 56 to be floated on the stored water W1. That is, the horizontal guide rail 55, the horizontal stage 60, and the arm portion 61 constitute the slice handling mechanism 14.

Additionally, in addition to the horizontal stage 60, the horizontal guide rail 55 is mounted with a horizontal stage 65 capable of moving along the horizontal guide rail 55. The horizontal stage 65 is capable of moving in a horizontal direction and of rotating about a Z axis. The horizontal stage 65 is mounted with a slide glass gripping robot 66 which is rotatable about one axis perpendicular to a Z direction. Additionally, the slide glass gripping robot 66 includes a pair of arm portions 66a which is disposed in parallel to each other while being away from each other by a predetermined distance and is capable of moving close to each other or away from each other.

It is possible to manufacture the thin slice specimen H in such a manner that the unused slide glass G is gripped from the slide glass containing shelf 57 and the thin slice B1 floated on the reservoir 56 is transferred onto the gripped slide glass G by appropriately operating the horizontal stage 65 and the slide glass gripping robot 66. Further, it is possible to contain the manufactured thin slice specimen H in the containing shelf 58. This containing process will be described later in detail.

The horizontal guide rail 55, the horizontal stage 65, and the slide glass gripping robot 66 described above constitute the slide glass handling robot 5. Additionally, in the present embodiment, the horizontal guide rail 55 constitutes both the slice handling mechanism 14 and the slide glass handling robot 5.

Figure 3:
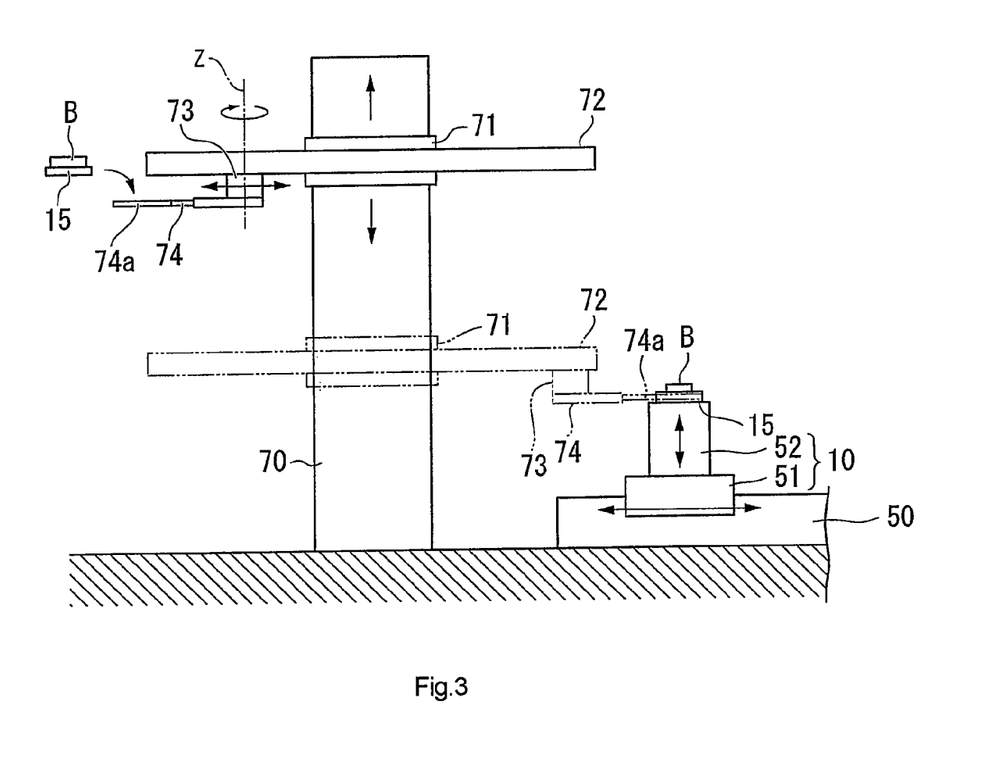
FIG. 3 is a side diagram showing a block handling robot of the automatic thin slice specimen manufacturing apparatus shown in FIG. 1.
Figure 4:
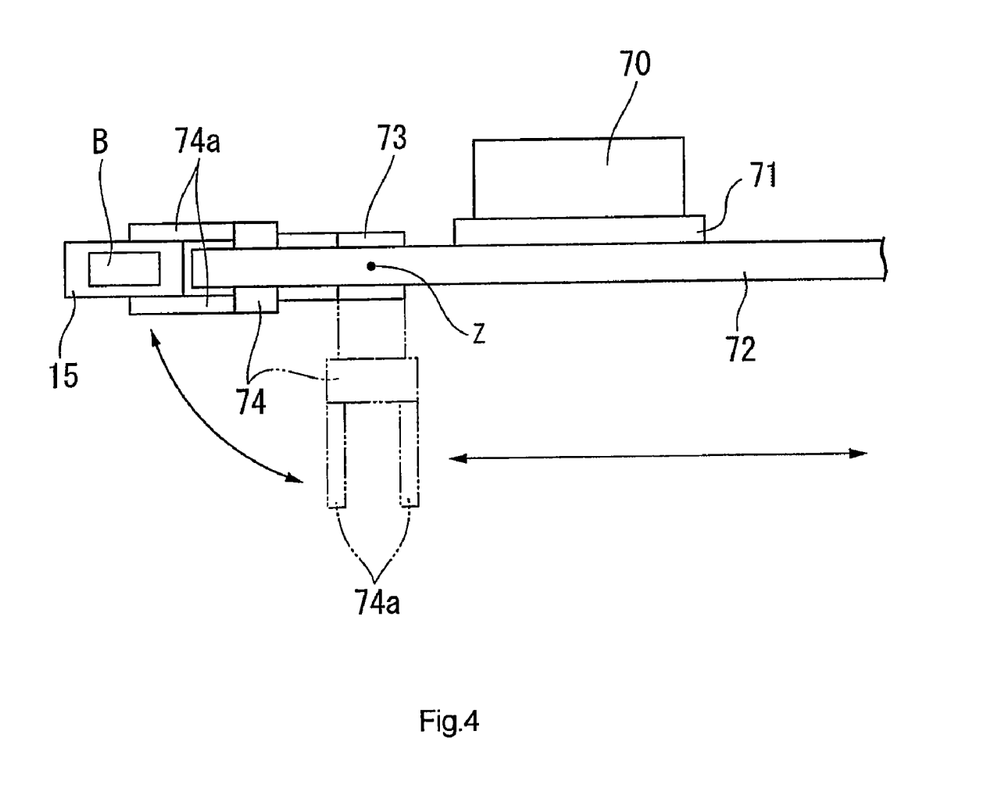
FIG. 4 is a top diagram showing the block handling robot shown in FIG. 3.

Additionally, as shown in FIGS. 1, 3, and 4, a Z-axis guide rail 70 extending in a Z direction is mounted to a portion on the opposite side of the reservoir 56 and adjacent to the guide rail 50. The Z-axis guide rail 70 is mounted with an elevation stage 71 capable of moving along the Z-axis guide rail 70. Additionally, the elevation stage 71 is mounted with a horizontal guide rail 72 extending in a horizontal direction. Then, the horizontal guide rail 72 is mounted with a horizontal stage 73 capable of moving along the horizontal guide rail 72. Additionally, the horizontal stage 73 is capable of moving in a horizontal direction and of rotating about a Z axis.

Additionally, the horizontal stage 73 is mounted with a gripping robot 74 having a pair of arm portions 74a which is disposed in parallel while being away from each other by a predetermined distance and capable of moving close to each other or away from each other. Then, it is possible to carry the embedded block B onto the fixed table 10 by appropriately operating the elevation stage 71, the horizontal stage 73, and the gripping robot 74. This carrying process will be described later in detail. The Z-axis guide rail 70, the elevation stage 71, the horizontal guide rail 72, the horizontal stage 73, and the gripping robot 74 described above serve as the block handling robot 2.

Incidentally, as shown in FIG. 1, the temperature sensor 80 for measuring the surface temperature of the embedded block B when the embedded block B is located at the standby position is provided on the front end side of the guiding pipe 40. The temperature sensor 80 is, for example, a non-contact sensor for measuring the surface temperature of the embedded block B, and outputs the measurement result to the temperature controllers 27 and 43.

Additionally, the guide rail 50 is provided with a position sensor 81 for determining whether the embedded block B is located at the standby position. The position sensor 81 is, for example, an optical sensor for detecting a position, and outputs the measurement result to the controller 82. Meanwhile, the controller 82 starts to operate the vapor generating mechanism 20 upon receiving a signal from the position sensor 81, the signal indicating a state that the embedded block B is located at the standby position. That is, the controller 82 operates the air supply source 35 and the opening-closing controller 36.

Additionally, after a predetermined elapsed time from when the controller 82 starts to operate the vapor generating mechanism 20, the controller 82 controls the cutting mechanism 13 to move the fixed table 10 from the standby position. Accordingly, it is possible to manufacture the thin slice B1 after reliably humidifying the embedded block B.

Next, a case will be described hereinafter in which a plurality of thin slice specimens H is manufactured from the embedded block B by the automatic thin slice specimen manufacturing apparatus 1 with such a configuration.

First, an operator positions the embedded block B at a position between the pair of arm portions 74a constituting the gripping robot 74 of the block handling robot 2. Then, as shown in FIG. 4, the gripping robot 74 receives the embedded block B from the operator by sandwiching the cassette 15 on which the embedded block B is placed by the use of the pair of arm portions 74a. Then, after the block handling robot 2 receives the embedded block B, as shown in FIG. 3, the block handling robot 2 carries the embedded block B to the fixed table 10 to be placed thereon by appropriately operating the elevation stage 71 and the horizontal stage 73 while sandwiching the cassette 15.

When the embedded block B is placed on the fixed table 10, the X-stage 51 moves so as to set the embedded block B at the standby position. At the same time, the horizontal stage 60 of the slice handling mechanism 14 moves along the horizontal guide rail 55, and the front end of the arm portion 61 is located at a position in the vicinity of a cutting start position of the embedded block B in a standby state.

Incidentally, when the embedded block B is set at the standby position, the position sensor 81 determines that the embedded block B is set at the standby position and outputs the position information to the controller 82. The controller 82 receives the information, and operates the air supply source 35 and the opening-closing controller 36.

Then, since the air supply source 35 starts to supply air to the inside of the pipe 28, and the opening-closing controller 36 controls the electromagnetic valve 37 to be in an open state so that the supplied air is sent to the front end of the pipe 28. Then, when the supplied air arrives at the front end via the pipe 28, the supplied air is discharged to the outside via the countless minute openings 28a. Accordingly, the countless bubbles V are generated under water stored in the tank 25. Since the countless bubbles V contact with the peripheral water (liquid) W2, an air-liquid interface is formed therebetween. At this time, since the water (liquid) W2 is heated by the heater 26, the water W2 evaporates in the gas in the bubbles V via the air-liquid interface to thereby humidify the gas. Particularly, since the size of each of the bubbles V is small and the surface area thereof becomes large relative to the volume, the gas in the bubbles V is approximately humidified up to the saturated vapor pressure in a short time. For this reason, when the countless bubbles V bounce on the water surface, the vapor E heated at a predetermined temperature is generated in the tank 25.

Figure 5:
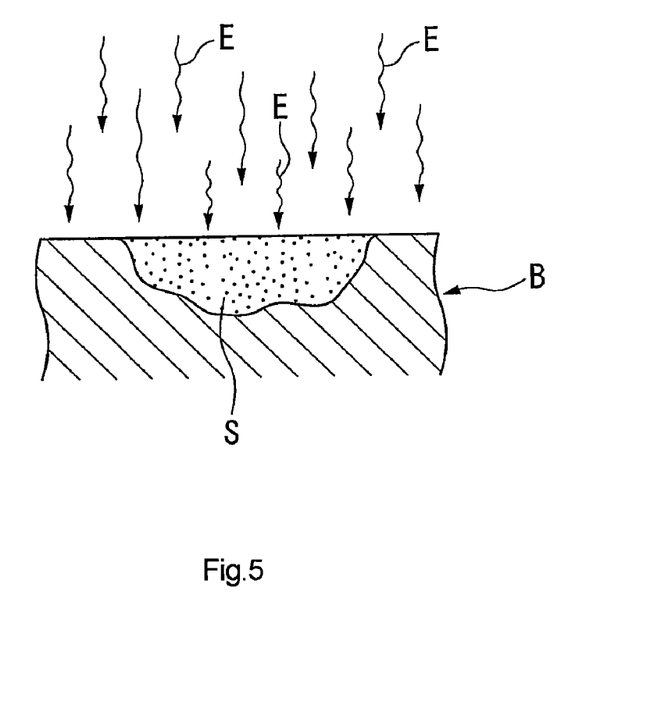
FIG. 5 is a diagram showing a state where a surface of the embedded block is exposed to vapor by an embedded block humidifier constituting the automatic thin slice manufacturing apparatus shown in FIG. 1.
Figure 6:
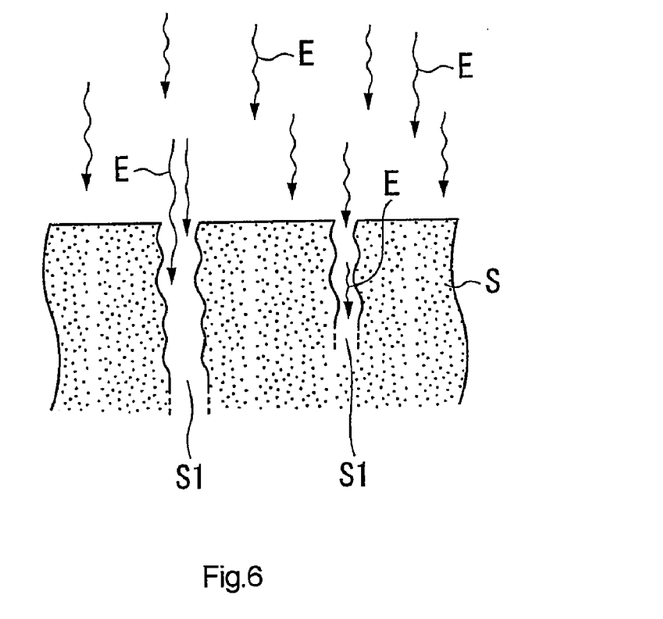
FIG. 6 is an enlarged diagram showing a surface of the embedded block shown in FIG. 5 and a state where vapor enters into a minute gap formed in a surface of a biological tissue.

Meanwhile, the vapor E generated in the tank 25 is guided to the front end of the guiding pipe 40 via the guiding pipe 40 and is guided to the embedded block B. Accordingly, as shown in FIG. 5, it is possible to spray the vapor E to the embedded block B so as to contact with the surface thereof. Particularly, unlike the mist used in the related art, since the embedded block B is exposed to the vapor E as gas, as shown in FIG. 6, the vapor E easily enters into a minute gap S1 formed in the surface of the biological tissue S in which moisture is replaced with paraffin. At this time, since the vapor E is heated at a predetermined temperature, when the vapor E enters into the gap S1 and contacts with the biological tissue S, the vapor E therein becomes a condensed state. Accordingly, it is possible to wet the biological tissue S from the inside. As a result, it is possible to humidify the embedded block B.

Particularly, since the vapor E as gas is used, even when the gap S1 is minute, it is possible to reliably allow the vapor E to enter into the gap S1. Accordingly, it is possible to humidify the embedded block B in a short time. Additionally, since the vapor E enters into the gap S1, it is possible to sufficiently carry out the humidification by the use of a small amount of vapor E. Accordingly, it is possible to prevent a problem of the related art that the temperature reduction of the embedded block B caused by the excessive evaporation of mist occurs. Also, it is possible to continuously humidify the embedded block B in an optimal state while preventing the thermal contraction of the embedded block B.

Particularly, during a time when the above-described humidification is carried out, the temperature sensor 80 accurately measures the surface temperature of the embedded block B and outputs the temperature information to the temperature controllers 27 and 43. The temperature controller 27 controls the temperature of the water W2 stored in the tank 25 so that the temperature of the vapor E more increases than the temperature of the embedded block B by 2° C. or so by controlling the heating amount of the heater 26 on the basis of the surface temperature of the embedded block B. Accordingly, it is possible to prevent a case in which the embedded block B is exposed to the vapor E having a temperature larger than the temperature of the embedded block B. As a result, it is possible to reliably humidify the embedded block B by the use of the vapor E while restricting a temperature variation of the embedded block B.

Additionally, in the same manner, the opening-closing controller 36 constituting the air controller 30 controls the air supply amount by controlling an opening degree of the electromagnetic valve 37 on the basis of the surface temperature of the embedded block B output from the temperature sensor 80. That is, the opening-closing controller 36 controls the generated amount of the vapor E. For this reason, it is possible to prevent a case in which the embedded block B is too much exposed to the excessive vapor E and hence the temperature thereof varies. Accordingly, for this reason, it is possible to efficiently restrict the temperature variation of the embedded block B.

Further, since the guiding pipe 40 guiding the vapor E to the embedded block B is heated by the heater 41, it is possible to heat the vapor E passing therethrough. Accordingly, even when the guiding pipe 40 is configured as a long pipe, it is possible to prevent a case in which the temperature of the vapor E becomes lower than the temperature of the embedded block B during a time when the vapor E is guided to the embedded block B, and thus to guide the vapor E to the embedded block B while keeping the temperature of the vapor E upon being generated in the tank 25. Accordingly, it is possible to freely design the guiding pipe 40 and to reliably humidify the embedded block B.

Additionally, since the vapor generating mechanism 20 is operated upon receiving the signal output from the position sensor 81, it is possible to promptly humidify the embedded block B located at the standby position B and to prevent the vapor generating mechanism 20 from being operated meaninglessly. Accordingly, it is possible to save power and thus to easily reduce running cost.

As described above, the embedded block B located at the standby position is humidified by the embedded block humidifier 11 in an optimal state where a temperature variation hardly occurs.

Then, after a predetermined elapsed time from a time point when the controller 82 starts to operate the vapor generating mechanism 20, the controller 82 moves the X-stage 51 along the guide rail 50 from the standby position toward the cutting blade 12 so that the embedded block B is cut by the cutting blade 12 into a sheet-like slice having a predetermined thickness (for example, 5 μm). Accordingly, the thin slice B1 is cut from the embedded block B.

Meanwhile, the arm portion 61, having the front end located in the vicinity of the cutting start position of the embedded block B in a standby state, adsorbs the thin slice B1 cut from the embedded block B by the cutting blade 12 in terms of static electricity. Then, the horizontal stage 60 mounted with the arm portion 61 moves along the horizontal guide rail 55 in accordance with the movement of the X-stage 51. Accordingly, it is possible to reliably adsorb the thin slice B1 by the use of the front end of the arm portion 61 without applying an external force to the thin slice B1.

After the front end of the arm portion 61 adsorbs the thin slice B1, the slice handling mechanism 14 carries the thin slice B1 by moving the horizontal stage 60. Then, when the arm portion 61 arrives at a position above the reservoir 56 constituting the extending mechanism 4, the arm portion 61 moves down in a Z direction so as to insert the front end into the water W1. Accordingly, the thin slice B1 adsorbed to the front end of the arm portion 61 is released to be thereby floated on the water W1. When the thin slice B1 is floated on the water W1, wrinkling or rounding thereof generated during the cutting process is removed in terms of surface tension, thereby extending the thin slice B1.

Meanwhile, in accordance with the cutting process and the carrying process of the thin slice B1, the slide glass handling robot 5 extracts one sheet of the unused slide glass G from the slide glass accommodating shelf 57 to be located at a position above the reservoir 56 by appropriately operating the horizontal stage 65 and the slide glass gripping robot 66.

That is, first, the pair of arm portions 66a of the slide glass gripping robot 66 is inserted in the slide glass accommodating shelf 57 by appropriately operating the horizontal stage 65 and the slide glass gripping robot 66. Subsequently, one sheet of the unused slide glass G is fixed and interposed between the pair of arm portions 66a by operating the pair of arm portions 66a to be close to each other. Subsequently, the slide glass G is extracted and is moved to a position above the reservoir 56 by appropriately operating the horizontal stage 65 and the slide glass gripping robot 66 with the slide glass G interposed between the pair of arm portions 66a. Subsequently, in this state, the slide glass G is located at a position above the reservoir 56 in a standby state until the thin slice B1 is carried to the inside of the reservoir 56.

Subsequently, as describe above, the thin slice B1 is carried to the inside of the reservoir 56 to be floated on the water W1. After a predetermined elapsed time, as shown in FIG. 1, the slide glass handling robot 5 lifts up the thin slice B1 floated on the water W1 by the use of the gripped slide glass G by appropriately operating the horizontal stage 65 and the slide glass gripping robot 66. Accordingly, the thin slice B1 is transferred onto the slide glass G. As a result, the thin slice specimen H is manufactured. Finally, the slide glass handling robot 5 carries the manufactured thin slice specimen H to the containing shelf 58 so as to be stored in the containing shelf 58.

As described above, with the automatic thin slice specimen manufacturing apparatus 1 according to the present embodiment, it is possible to automatically manufacture the thin slice specimen H from the embedded block B and to store the thin slice specimen H in the containing shelf 58. Accordingly, it is possible to reduce a burden of the operator. Additionally, it is possible to automatically manufacture a necessary sheet of thin slice B1 from one embedded block B by reciprocating the X-stage 51 along the X-guide rail 50 and to manufacture the thin slice specimen H.

Additionally, upon ending a process in which a necessary sheet of thin slice B1 is manufactured, the block handling robot 2 carries the used embedded block B from the fixed table 10. Accordingly, the operator is capable of exchanging the used embedded block B with a new next embedded block B. Then, it is possible to automatically manufacture a predetermined sheet of thin slice specimen H from the next embedded block B by repeating the above-described process.

Particularly, since the automatic thin slice specimen manufacturing apparatus 1 according to the present embodiment is provided with the automatic thin slice manufacturing device 3 having the embedded block humidifier 11, it is possible to manufacture the thin slice B1 from the embedded block B humidified in an optimal state where a temperature variation hardly occurs. For this reason, it is possible to manufacture the thin slice B1 having a uniform thickness as much as possible by restricting a deviation in thickness. Accordingly, it is possible to manufacture the high-quality thin slice B1. Additionally, since it is possible to humidify the embedded block B located at the standby position in a short time, it is possible to reduce time necessary for the humidification and thus to improve a throughput.

Additionally, since the thin slice specimen H is manufactured by the use of the high-quality thin slice B1, it is possible to manufacture the high-quality thin slice specimen H. Accordingly, it is possible to more improve precision upon carrying out various experiments and tests using the thin slice specimen H.

Second Embodiment

Next, a second embodiment of the invention will be described with reference to FIGS. 7 to 11. Additionally, in the second embodiment, the same reference numerals are given to the same components as those of the first embodiment, and the description thereof will be omitted.

The second embodiment is different from the first embodiment as follows. The first embodiment has a configuration that the vapor E generated by the vapor generating mechanism 20 is guided to the embedded block B, but the second embodiment has a configuration that the vapor E generated by the vapor generating mechanism 20 is temporarily collected and accumulated, and a certain accumulated amount of vapor E is guided at a time.

Figure 7:
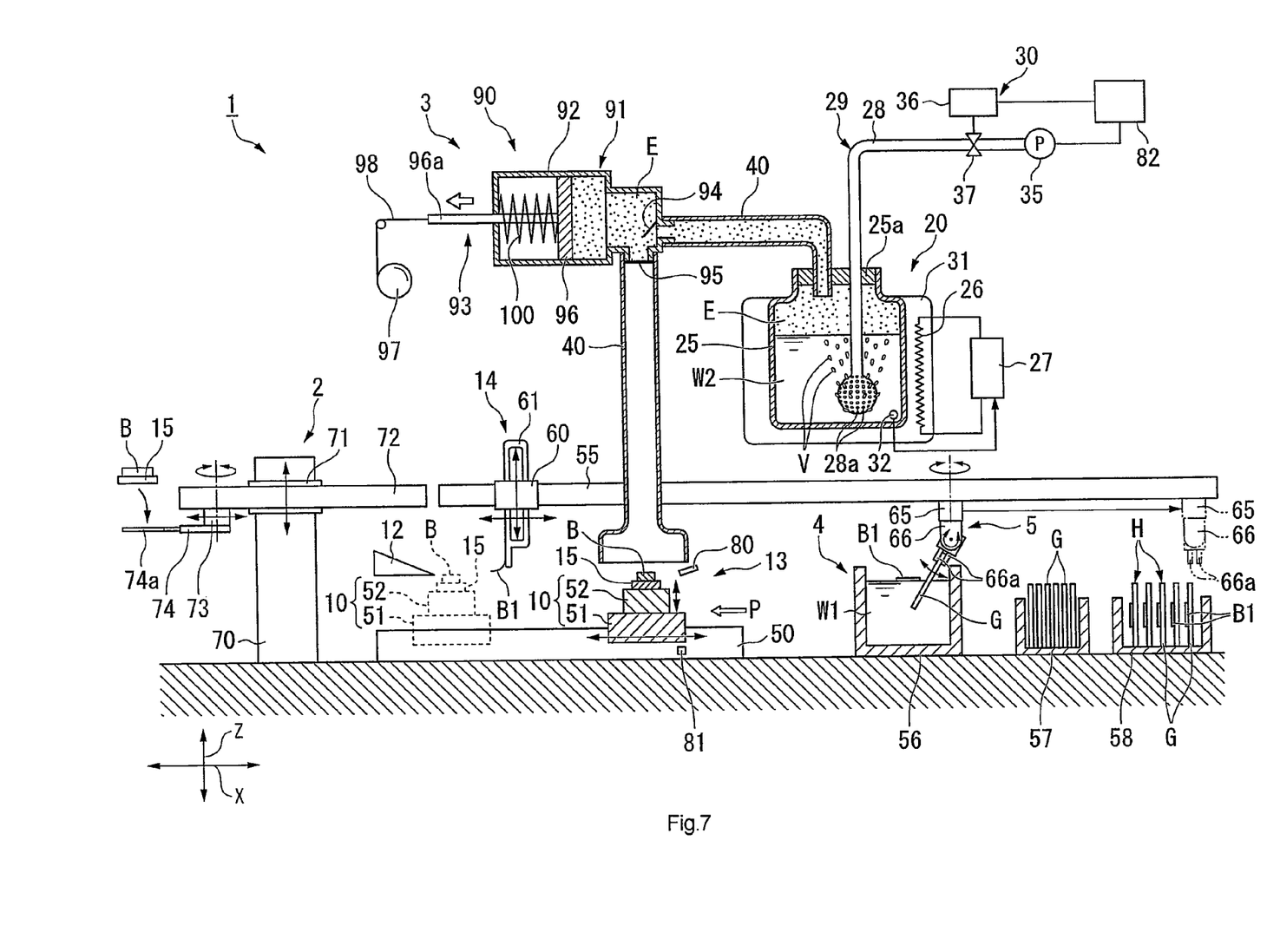
FIG. 7 is a configuration diagram showing the automatic thin slice specimen manufacturing apparatus according to a second embodiment of the invention.
Figure 8:
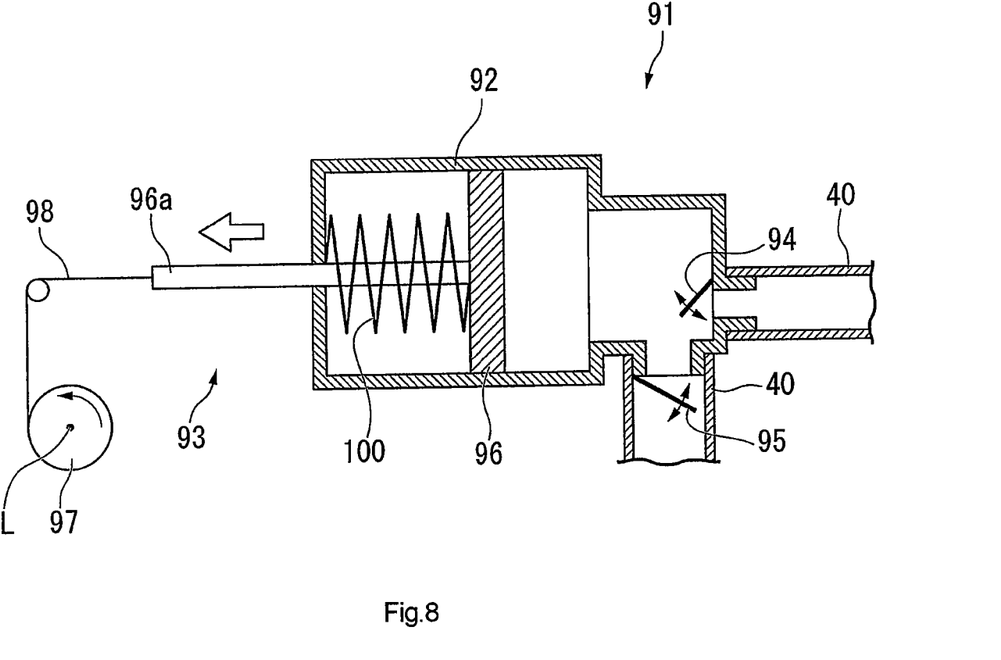
FIG. 8 is a partially enlarged diagram showing the embedded block humidifier constituting the automatic thin slice specimen manufacturing apparatus shown in FIG. 7.

That is, as shown in FIGS. 7 and 8, an embedded block humidifier 90 according to the present embodiment includes an guiding mechanism 91 provided with an accumulating part 92 for temporarily accumulating the vapor E and a discharging mechanism 93 for discharging the accumulated vapor E to the outside of the accumulating part 92 at a time.

The accumulating part 92 is a cylindrical cylinder, and is mounted to a portion in the course of the guiding pipe 40. Specifically, one end of the accumulating part 92 is connected to the guiding pipe 40 inserted into the tank 25 and the guiding pipe 40 extending to a position in the vicinity of the embedded block B. That is, the vapor E generated by the vapor generating mechanism 20 flows from the tank 25 to the inside of the accumulating part 92 to be accumulated therein. Then, the collected vapor E is extruded by the discharging mechanism 93 from the inside of the accumulating part 92 to the guiding pipe 40 extending to a position in the vicinity of the embedded block B, thereby being guided toward the embedded block B.

At this time, the connection portion between the accumulating part 92 and the guiding pipe 40 is provided with valves 94 and 95 for regulating the flow of the vapor E in one direction. Here, the valve 94 provided in the connection portion between the accumulating part 92 and the guiding pipe 40 inserted to the tank 25 allows the vapor E to flow into the accumulating part 92 and regulates the leakage of the vapor E from the accumulating part 92 to the tank 25. Accordingly, it is possible to reliably allow the vapor E to flow into the accumulating part 92 and to prevent the accumulated vapor E from reversely flowing to the tank 25 upon discharging the accumulated vapor E.

On the other hand, the valve 95 provided in the connection portion between the accumulating part 92 and the guiding pipe 40 extending to a position in the vicinity of the embedded block B allows the vapor E to leaks from the accumulating part 92 to the embedded block B and regulates the inflow of the vapor E from the outside to the inside of the accumulating part 92. Accordingly, it is possible to reliably accumulate the vapor E in the accumulating part 92 and to reliably discharge the accumulated vapor E to the embedded block B.

Figure 9:
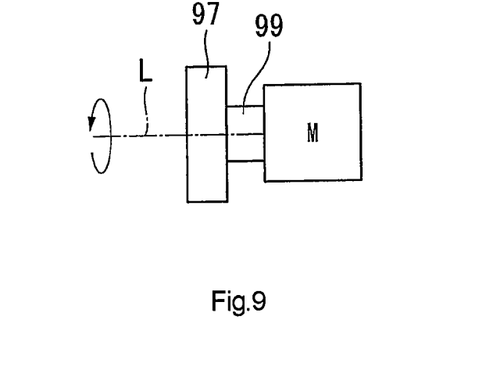
FIG. 9 is a diagram showing a relationship of a motor, a clutch, and a pulley constituting the embedded block humidifier shown in FIG. 8.

The accumulating part 92 with such a configuration contains a movable piston 96 in which a piston shaft 96a is inserted from the other end side of the accumulating part 92. As shown in FIGS. 8 and 9, the piston shaft 96a is connected to a wire 98 wound on a pulley 97 rotating about a rotary shaft L upon driving a motor M. Accordingly, when the motor M is rotationally driven, it is possible to collect the vapor E in the inside of the accumulating part 92 by pulling backward the piston 96. Additionally, the accumulating part 92 is capable of accumulating the vapor E of 1 to 5 L or so.

Incidentally, a clutch 99 is provided between the motor M and the pulley 97 so as to be capable of disconnecting the connection therebetween, and hence the pulley 97 is capable of being separated from the motor M at arbitrary timing. Additionally, a coil spring 100 is provided between the piston 96 and the accumulating part 92, and the piston 96 is urged toward one end of the accumulating part 92 at a normal time. Accordingly, when the pulley 97 is separated from the motor M, it is possible to push the piston 96 toward one end of the accumulating part 92 in terms of an elastic force of the coil spring 100. Accordingly, it is possible to discharge the vapor E accumulated in the inside of the accumulating part 92 to the outside of the accumulating part 92 at a time.

That is, the piston 96, the pulley 97, the wire 98, the motor M, the clutch 99, and the coil spring 100 described above serve as the discharging mechanism 93 for discharging the accumulated vapor E to the outside of the accumulating part 92 at a time.

Additionally, the controller 82 according to the present embodiment controls the operation timing of the motor M or the separation timing between the motor M and the pulley 97 in terms of the clutch 99.

In the embedded block humidifier 90 with such a configuration, the controller 82 operates the air supply source 35 and the opening-closing controller 36 before the embedded block B is set at the standby position. Then, the air supply source 35 starts to supply air to the inside of the pipe 28 and the opening-closing controller 36 controls the electromagnetic valve 37 to be in an open state so as to send the supplied air to the front end of the pipe 28. Accordingly, as shown in FIG. 7, the vapor E is generated in the tank 25 and flows to the guiding pipe 40.

At the same time, the controller 82 drives the motor M so as to rotate the pulley 97. Then, since the wire 98 starts to be wound, the piston 96 is pulled backward in terms of the piston shaft 96a so as to move to the other side of the accumulating part 92. At this time, it is desirable that a pulling speed of the piston 96 is approximately the same as the flow rate (for example, 1 to 5 L/min) of the generated vapor E.

When the piston 96 is pulled backward, the vapor E flows into the accumulating part 92 from the guiding pipe 40 inserted in the tank 25. Accordingly, it is possible to temporarily accumulate the vapor E in the accumulating part 92. Then, when the piston 96 is pulled backward as much as the volume of the accumulating part 92, the controller 82 stops the motor M and closes the electromagnetic valve 37. Additionally, since the inside of the accumulating part 92 is a slight negative-pressure state, the valve 95 is closed. For this reason, the accumulated vapor E cannot leak to the outside.

In this state, when the embedded block B is set at the standby position, the controller 82 disconnects the connection between the motor M and the pulley 97 by separating the clutch 99. Then, since the piston 96 is urged by the elastic force of the coil spring 100, the piston 96 is pushed toward one end of the accumulating part 92 at a time. Accordingly, the accumulated vapor E is discharged to the outside of the accumulating part 92 at a time via the valve 95. Additionally, at this time, since the valve 94 is closed, the vapor E cannot flow in an inverse direction to the tank 25.

Then, the discharged vapor E is guided to the embedded block B via the guiding pipe 40. Accordingly, since it is possible to supply the vapor E accumulated up to a certain degree to the embedded block B, it is possible to carry out the humidification in a shorter time. Accordingly, it is possible to improve the throughput and thus to more efficiently manufacture the thin slice than the first embodiment.

Additionally, in the present embodiment, it is desirable that the accumulating part 92 is insulated as much as possible in such a manner that the accumulating part 92 is made from material having low thermal conductivity or the accumulating part 92 is covered by heat-insulating material. Accordingly, it is possible to prevent a temperature reduction of the vapor E as much as possible upon accumulating the vapor E.

Further in the second embodiment, like the first embodiment, the rubber heater 42 provided with the heater 41 may be provided in the course of the guiding pipe 40 (between the accumulating part 92 and the tank 25).

In the second embodiment, the cylinder type is exemplified as an example of the accumulating part 92, but the invention is not limited thereto.

Figure 10:
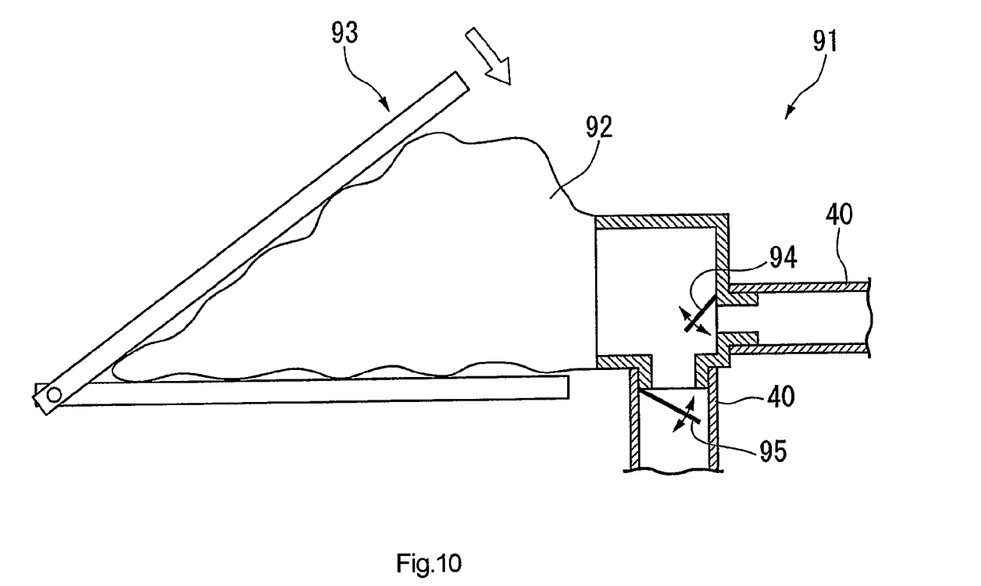
FIG. 10 is a diagram showing a modified example of the embedded block humidifier shown in FIG. 8.

For example, as shown in FIG. 10, the accumulating part 92 may be configured as a flexible accommodating member. Even in this case, it is possible to accumulate the vapor E therein. Additionally, in this case, the discharging mechanism 93 may be configured to crush the accumulating part 92 as the accommodating member in an interposed state. Accordingly, it is possible to discharge the accumulated vapor E at a time. Therefore, it is possible to exhibit the same effect and advantage.

Figure 11:
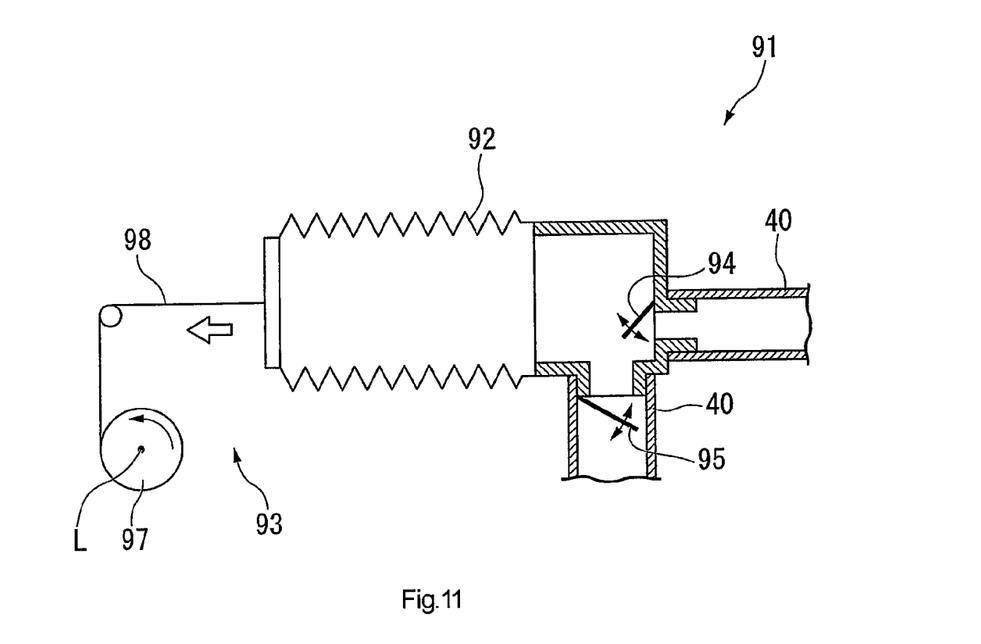
FIG. 11 is a diagram showing another modified example of the embedded block humidifier shown in FIG. 8.

Further, as shown in FIG. 11, the accumulating part 92 may be formed into a bellows shape so as to extend in an axial direction. In this case, it is possible to accumulate the vapor E in the accumulating part 92 by pulling the other end of the accumulating part 92 in terms of the wrier 98. Then, when the motor M is disconnected from the pulley 97 by separating the clutch 99, the accumulating part 92 contracts of itself by a contraction force of the bellows, thereby discharging the accumulated vapor E at a time. Accordingly, it is possible to exhibit the same effect and advantage.

Additionally, the technical scope of the invention is not limited to the above-described embodiments, but may be modified into various forms within a scope not departing from the spirit of the invention.

For example, in the respective embodiments, the extending mechanism 4 is configured as the reservoir 56 for storing the water W1, but the invention is not limited thereto. For example, the extending mechanism 4 may be configured by a reservoir for being adjacent to the reservoir 56 and storing warm water and a hot plate.

In this case, the thin slice B1 subjected to the extending process using water is placed on the slide glass G and the thin slice B1 is carried to the reservoir storing warm water to be floated on the warm water by the use of the slide glass handling robot 5. Since the thin slice B1 is easily extended in terms of the extending process using warm water, it is possible to remove the remaining wrinkling or rounding not completely removed during the extending process using the water W1. Accordingly, it is possible to manufacture the thin slice specimen H having higher quality.

Further, it is possible to more heat the thin slice B1 via the slide glass G in such a manner that the slide glass G having the thin slice B1 placed thereon is placed on the hot plate after the extending process using warm water. Accordingly, it is possible to more remove the wrinkling or rounding not completely removed during the extending process using warm water. Likewise, it is more desirable that the reservoir storing the warm water and the hot plate are provided in that the thin slice specimen H having higher quality is manufactured.

What is claimed is:

1. An embedded block humidifier for humidifying an embedded block having a biological specimen embedded in an embedding agent, the embedded block humidifier comprising:
    a vapor generating mechanism generating vapor heated at a predetermined temperature;
    a guiding mechanism guiding the vapor to the embedded block so that the generated vapor contacts with a surface of the embedded block set at a predetermined standby position;
    a tank storing liquid;
    a liquid heater heating the liquid;
    a heater temperature controller controlling a temperature of the liquid heater;
    a bubble generating mechanism provided with a pipe inserted into the tank to be submerged in the liquid and generating countless bubbles from the front end of the pipe by supplying air to the pipe; and
    an air controller controlling an air supply amount.

2. The embedded block humidifier according to claim 1, further comprising:
    a sensor measuring a surface temperature of the embedded block,
    wherein the heater temperature controller controls the temperature of the liquid heater so that a temperature of the generated vapor more increases than a temperature of the embedded block measured by the sensor by a predetermined temperature.

3. The embedded block humidifier according to claim 2, wherein the air controller controls the air supply amount on the basis of the temperature of the embedded block measured by the sensor.

4. The embedded block humidifier according to claim 1, wherein the guiding mechanism includes:
   a guiding pipe guiding the vapor to the embedded block;
   a guiding-pipe heater heating the guiding pipe; and
   a guiding-pipe temperature controller controlling a temperature of the guiding-pipe heater.

5. The embedded block humidifier according to claim 1, wherein the guiding mechanism includes:
   an accumulating part temporarily accumulating the vapor; and
   a discharging mechanism discharging the accumulated vapor to the outside of the accumulating part at a time, and
   wherein the guiding mechanism guides the discharged vapor to the embedded block.

6. An automatic thin slice manufacturing device comprising:
   the embedded block humidifier comprising:
      a vapor generating mechanism generating vapor heated at a predetermined temperature; and
      a guiding mechanism guiding the vapor to the embedded block so that the generated vapor contacts with a surface of the embedded block set at a predetermined standby position;
   a fixed table placing and fixing the embedded block thereon;
   a cutting mechanism provided with a cutting blade disposed at a position away from the standby position and cutting the embedded block by moving the fixed table between the standby position and the cutting blade so as to obtain a thin slice having a predetermined thickness; and
   a thin slice carrying mechanism carrying the cut thin slice.

7. The automatic thin slice manufacturing device according to claim 6, further comprising:
   a position sensor determining whether the embedded block is located at the standby position; and
   a controller operating the vapor generating mechanism when the position sensor determines that the embedded block is located at the standby position.

8. The automatic thin slice manufacturing device according to claim 6, wherein the cutting mechanism moves the fixed table after a predetermined elapsed time from a time point when the vapor generating mechanism is operated.

9. An automatic thin slice specimen manufacturing apparatus comprising:
   the automatic thin slice manufacturing device according to claim 6;
   a block carrying mechanism carrying the embedded block onto the fixed table;
   an extending mechanism extending the thin slice carried by the thin slice carrying mechanism by floating the thin slice on at least liquid; and
   a transferring mechanism manufacturing a thin slice specimen by transferring the extended thin slice onto a substrate.

* * * * *